(12) United States Patent
Kamiya et al.

(10) Patent No.: US 9,029,568 B2
(45) Date of Patent: May 12, 2015

(54) BRANCHED HETERO POLYFUNCTIONAL POLYOXYALKYLENE COMPOUND AND INTERMEDIATE THEREOF

(71) Applicant: NOF Corporation, Tokyo (JP)

(72) Inventors: Masaki Kamiya, Kanagawa (JP); Ken-ichiro Nakamoto, Kanagawa (JP)

(73) Assignee: NOF Corporation, Tokyo (JP)

( * ) Notice: Subject to any disclaimer, the term of this patent is extended or adjusted under 35 U.S.C. 154(b) by 0 days.

(21) Appl. No.: 13/632,353

(22) Filed: Oct. 1, 2012

(65) Prior Publication Data

US 2013/0172576 A1   Jul. 4, 2013

(30) Foreign Application Priority Data

Sep. 30, 2011   (JP) .................. 2011-216120

(51) Int. Cl.
| | | |
|---|---|---|
| *C07D 403/14* | (2006.01) | |
| *C07C 211/10* | (2006.01) | |
| *C07C 217/08* | (2006.01) | |
| *C07C 43/205* | (2006.01) | |
| *C07D 207/36* | (2006.01) | |
| *C07D 207/46* | (2006.01) | |
| *C08G 65/08* | (2006.01) | |

(52) U.S. Cl.
CPC ............. *C07C 217/08* (2013.01); *C07C 43/205* (2013.01); *C07D 207/36* (2013.01); *C07D 207/46* (2013.01); *C08G 65/08* (2013.01)

(58) Field of Classification Search
CPC ............................ C07D 403/14; C07C 211/10
USPC ........................................ 548/456; 564/505
See application file for complete search history.

(56) References Cited

U.S. PATENT DOCUMENTS

| | | | |
|---|---|---|---|
| 6,153,655 A | 11/2000 | Martinez et al. | |
| 6,251,382 B1 | 6/2001 | Greenwald et al. | |
| 6,824,766 B2 | 11/2004 | Greenwald et al. | |

FOREIGN PATENT DOCUMENTS

WO   2005/061005 A2   7/2005

OTHER PUBLICATIONS

Yamashita, et al. (document No. 126:252599), retrieved from CAPLUS; Feb. 10, 1997.*
Wallace, et al. Document No. 136:374762, retrieved from CAPLUS; 2001.*
Maekawa, et al. Document No. 123:342056, retrieved from CAPLUS; Jun. 21, 1995.*
Logan, et al. Document No. 131:5650, retrieved from CAPLUS; 1999.*

* cited by examiner

*Primary Examiner* — Shawquia Jackson
(74) *Attorney, Agent, or Firm* — Sughrue Mion, PLLC

(57) ABSTRACT

A branched hetero polyfunctional polyoxyalkylene compound represented by the following formula (1):

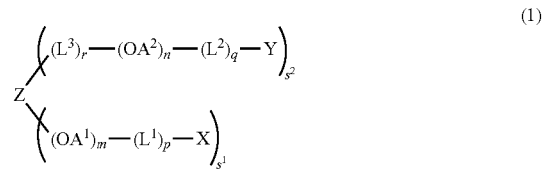

wherein Z represents a hydroxyl group-removed residue of pentaerythritol or dipentaerythritol, $OA^1$ and $OA^2$ represent an oxyalkylene group having 2 to 4 carbon atoms, $L^1$, $L^2$ and $L^3$ represent an alkylene group or an alkylene group that contains an ester bond, a urethane bond, an amide bond, an ether bond, a carbonate bond, a secondary amino group or a urea bond, X and Y are different from each other and represent a functional group capable of a chemical reaction; m and n are an average number of moles of the oxyalkylene group added, m represents 5 to 1,000, n represents 0 to 1,000, and p, q and r represent 0 or 1; and $s^1$ is an integer of 2 or more and $s^1+s^2=4$ or 6.

7 Claims, No Drawings

US 9,029,568 B2

BRANCHED HETERO POLYFUNCTIONAL POLYOXYALKYLENE COMPOUND AND INTERMEDIATE THEREOF

FIELD OF THE INVENTION

The present invention relates to a novel branched hetero polyfunctional polyoxyalkylene compound to be used in applications for modifying bio-related substances and a production intermediate of the polyoxyalkylene compound.

BACKGROUND OF THE INVENTION

Drug delivery systems have been increasingly applied to treatment of various diseases as ideal drug application forms. Of these, developments for improving circulation in blood by modifying drugs with polyethylene glycol have been widely performed and drugs obtained by modifying cytokines such as interferon and GCSF with polyethylene glycol have been placed on the market and have been widely used.

In general, as elimination paths of a drug applied into the body, there may be mentioned filtration excretion from kidney glomeruli and treatment by a reticuloendothelial system (RES system) represented by Kupper cell. Since the glomeruli function as a size-dependent filtration membrane, the filtration excretion path can be avoided by modifying the drug with a polyoxyalkylene to enlarge the size. Also, in the RES system, the drug is phagocytized by RES recognition through non-specific interaction (opsonization) but the polyoxyalkylene-modified compound exhibits a low interaction with a living body component, so that the RES recognition can be avoided. For such reasons, polyoxyalkylene derivatives have been widely used as DDS materials for elongating the circulation in blood.

Hitherto, as the polyoxyalkylene derivatives, a type of the derivatives having one reactive functional group at a terminal end of methoxypolyethylene glycol is common but recently, there has been developed a hetero polyfunctional polyoxyalkylene derivative having different reactive functional groups at both terminal ends and a polyoxyalkylene derivative having two proximate reactive functional groups (M. J. Roberts et al./Chemistry for peptide and protein PEGylation/Advanced Drug Delivery Reviews 54 (2002) 459-476). Since such derivative has two functional groups in proximate positions, it has effects that a metal atom is chelated, it acts as a pseudoantibody through bonding of an antibody fragment to each functional group, and an amount of a low-molecular-weight drug bonded can be increased. Moreover, since different reactive functional groups are present at both terminal ends, it is possible to introduce different molecules, for example, biofunctional molecules such as drug physiologically active substances and target-directing substances into individual terminal ends and thus the derivative has been used as a hetero crosslinker that crosslinks the biofunctional molecules each other or the biofunctional molecule and various drug carriers or devices.

Patent Document 1 discloses a structure wherein a branched chain and a drug are introduced into both terminal ends of polyethylene glycol via an amide bond. It is known that the circulation in blood, which is a characteristic of a polyoxyalkylene-modified compound, is improved as the molecular weight increases. On the other hand, when the molecular weight reaches a level of several tens of thousands, there is a problem that viscosity of a drug solution increases and drug design becomes difficult.

Patent Documents 2 and 3 disclose compounds obtained by activating a methoxypolyethylene glycol terminal end, subsequently reacting the terminal end with an amino group-containing core skeleton compound such as 1,3-diaminopropanol to introduce a polyethylene glycol chain via a urethane bond, and then introducing a plurality of functional groups into remaining hydroxyl groups.

Similarly, Patent Document 4 also discloses compounds obtained by activating a methoxypolyethylene glycol terminal end, subsequently reacting the terminal end with 2,3-diaminosuccinic acid protected with Boc group to introduce a polyethylene glycol chain via an amide bond, and then introducing a plurality of functional groups into remaining functional groups.

In the derivatives disclosed therein, a polyoxyalkylene chain and a core skeleton compound such as lysine are bonded via an amide bond, a carbamate bond, or an ester bond, but there is a problem that these bonds are liable to undergo hydrolysis during storage or during a reaction under alkaline conditions and, as a result, the polyoxyalkylene chain is dissociated.

Moreover, in the production thereof, since the production is performed via a step of reacting the core skeleton compound such as lysine with a reactive polyoxyalkylene derivative, there is a problem that impurities different in the introduced number of polyoxyalkylene chains are formed. It is industrially difficult to purify such polymeric compounds one another.

Furthermore, in each of the compounds disclosed in Patent Documents 2, 3 and 4, an asymmetric carbon is present in the core skeleton and there is a problem that the compound is not homogeneous when bonding to a drug and development to a medicament are considered.

Additionally, in the disclosed compounds, it is difficult to introduce different molecules, for example, biofunctional molecules such as drug physiologically active substances and target-directing substances into activated functional groups and thus it is difficult to further enhance the function of a polyethylene glycol-bonded compound.

Based on such background, there has been required a branched hetero polyfunctional polyoxyalkylene compound which has a high stability and facilitates achievement of homogeneity owing to the absence of an asymmetric carbon in the molecule.

BACKGROUND ART DOCUMENTS

Patent Documents

[Patent Document 1] U.S. Pat. No. 6,153,655
[Patent Document 2] U.S. Pat. No. 6,251,382
[Patent Document 3] U.S. Pat. No. 6,824,766
[Patent Document 4] International Publication No. 2005/061005

SUMMARY OF THE INVENTION

A problem to be solved by the invention is to provide a branched hetero polyfunctional polyoxyalkylene compound which is formed with stable bonds, is difficult to decompose into a single chain, has no asymmetric carbon in the core skeleton, and contains plurality of different kinds of functional groups.

As a result of the extensive studies for solving the above problems, the present inventors have obtained a novel branched hetero polyfunctional polyoxyalkylene compound having the following chemical structure.

Namely, the invention relates to the following:

(1) A branched hetero polyfunctional polyoxyalkylene compound represented by the following formula (1):

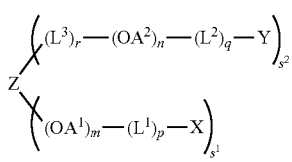

(1)

wherein Z represents a hydroxyl group-removed residue of pentaerythritol or dipentaerythritol, $OA^1$ and $OA^2$ are an oxyalkylene group having 2 to 4 carbon atoms, $L^1$, $L^2$ and $L^3$ are an alkylene group or an alkylene group that contains an ester bond, a urethane bond, an amide bond, an ether bond, a carbonate bond, a secondary amino group or a urea bond, $OA^1$ and $OA^2$ and $L^1$, $L^2$ and $L^3$ may be the same or different from one another in one molecule; X and Y are different from each other and represent a functional group capable of a chemical reaction; m and n are an average number of moles of the oxyalkylene group added, m represents 5 to 1,000, n represents 0 to 1,000, and p, q and r represent 0 or 1; and $s^1$ is an integer of 2 or more and $s^1+s^2=4$ or 6.

(2) The branched hetero polyfunctional polyoxyalkylene compound according to (1), wherein $OA^1$ and $OA^2$ are an oxyethylene group, in the formula (1).

(3) The branched hetero polyfunctional polyoxyalkylene compound according to (1) or (2), wherein n and r are 0 and m is 100 to 800, in the formula (1).

(4) The branched hetero polyfunctional polyoxyalkylene compound according to (1), wherein n is 1 to 500 and m is 100 to 800, in the formula (1).

(5) The branched hetero polyfunctional polyoxyalkylene compound according to any one of (1) to (4), wherein X and Y are a functional group capable of chemically bonding to an amino group, a mercapto group, a carboxyl group, an aldehyde group, an unsaturated bond, or an azido group, in the formula (1).

(6) The branched hetero polyfunctional polyoxyalkylene compound according to any one of (1) to (5), wherein X and Y are a functional group selected from a substituted active ester, an active carbonate, an aldehyde, an isocyanate, an isothiocyanate, an epoxide, a thiol, a substituted maleimide, a hydrazide, a dithiopyridine, a substituted sulfonate, an amine, an oxyamine, an α-haloacetyl, a carboxylic acid, a substituted unsaturated bond, and an azide, in the formula (1).

(7) The branched hetero polyfunctional polyoxyalkylene compound according to any one of (1) to (5), wherein, in the formula (1), X and Y are a functional group selected from the following:

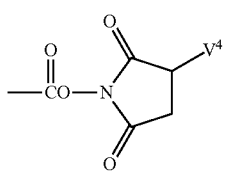

(a)

-continued

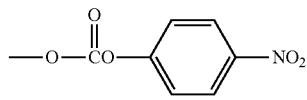

(b)

(c)

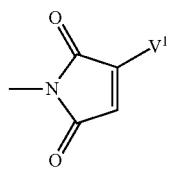

(d)

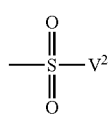

(e)

—COOH (f)

—SH (g)

(h)

(i)

—C≡C—V³ (j)

—NH₂ (k)

—O—NH₂ (l)

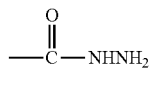

(m)

—N₃ (n)

wherein $V^1$ and $V^3$ represent a hydrocarbon group having 1 to 5 carbon atoms; $V^2$ represents a hydrocarbon group having 1 to 10 carbon atoms that may contain a halogen atom; and $V^4$ represents a hydrogen atom or a sulfonyl group.

(8) The branched hetero polyfunctional polyoxyalkylene compound according to (6), wherein at least one of X and Y is selected from the group consisting of a carboxylic acid, an amine, an oxyamine, and a thiol, in the formula (1).

(9) The branched hetero polyfunctional polyoxyalkylene compound according to (8), wherein $OA^1$ and $OA^2$ are an oxyalkylene group, n=1 and r=0, m is 100 to 800, Z is pentaerythritol, and $s^1=s^2=2$, in the formula (1).

(10) A polyoxyalkylene compound as a production intermediate of the compound represented by the formula (1) according to (1), represented by the following formula (2):

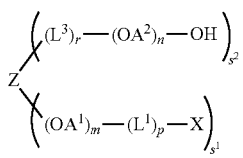

(2)

wherein Z represents a hydroxyl group-removed residue of pentaerythritol or dipentaerythritol, $OA^1$ and $OA^2$ are an oxyalkylene group having 2 to 4 carbon atoms, $L^1$ and $L^3$ are an alkylene group or an alkylene group that contains an ester bond, a urethane bond, an amide bond, an ether bond, a carbonate bond, a secondary amino group or a urea bond, $OA^1$ and $OA^2$ and $L^1$ and $L^3$ may be the same or different from one another in one molecule; X represent a functional group capable of a chemical reaction or a protected functional group; m and n are an average number of moles of the oxyalkylene group added, m represents 5 to 1,000, n represents 0 to 1,000, and p and r represent 0 or 1; and $s^1$ is an integer of 2 or more and $s^1+s^2=4$ or 6.

In the novel branched hetero polyfunctional polyoxyalkylene compound (1) according to the invention, the skeleton is all formed with stable ether bonds, so that the compound is difficult to decompose into a single chain and the branching point of the polyoxyalkylene chain is formed with a quaternary carbon, so that no asymmetric carbon is present in the core skeleton and homogeneity is high. Moreover, since it has different reactive functional groups at the terminal ends of the polyoxyalkylene chain, it can modify two kinds of different biofunctional molecules.

Furthermore, since the compound (1) can be produced by the method of performing polymerization of an alkylene oxide after the hydroxyl group of the core skeleton is selectively protected, the number of the polyoxyalkylene chains to be elongated can be controlled. Therefore, a polymeric impurity having a reactive functional group is hardly formed and thus the compound (1) is contaminated with little impurities, which are difficult to separate, and is particularly suitable for applications for modifying bio-related substances.

DETAILED DESCRIPTION OF THE INVENTION

The following will explain the present invention in detail.

In the formula (1) of the invention, Z is a hydroxyl group-removed residue of pentaerythritol or dipentaerythritol. In the case where Z is pentaerythritol, the compound is a bifunctional derivative wherein $s^1+s^2=4$, preferably $s^1=s^2=2$. In the case where Z is dipentaerythritol, $s^1+s^2=6$ but in preferred embodiments, the compound is a bifunctional derivative wherein $s^1=2$ and $s^2=4$ or a tetrafunctional derivative wherein $s^1=4$ and $s^2=2$.

In the formula (1), $OA^1$ and $OA^2$ represent an oxyalkylene group having 2 to 4 carbon atoms. Specifically, there may be mentioned an oxyethylene group, an oxypropylene group, an oxybutylene group, an oxytetramethylene group, and the like. $OA^1$ and $OA^2$ may be the same or different and, in the case where they are composed of two or more kinds of oxyalkylene groups, they may be one randomly added or one added in a block form. An oxyalkylene group having smaller number of carbon atoms has higher hydrophilicity, so that preferred are an oxyethylene group and an oxypropylene group and more preferred is an oxyethylene group.

In the formula, m and n are an average number of moles of the oxyalkylene group added. m is 5 to 1,000, preferably 10 to 1,000, further preferably 50 to 800, and most preferably 100 to 800. n is 0 to 1,000 and preferably 0 to 500. As a preferred embodiment, n is preferably 0. In other preferred embodiments, n is 1 to 3 and, as further preferred embodiments, n is 100 to 500.

In the formula, p, q and r represent 0 or 1.

In the formula, X and Y represent a group capable of chemically bonding to a bio-related substance, are an electrophilic functional group or a nucleophilic functional group, and are not particularly limited as far as they are a group capable of forming a covalent bond with a bio-related substance. For example, there may be mentioned functional groups described in "POLY(ETHYLENE GLYCOL) CHEMISTRY written by J. Milton Harris, "Bioconjugate Techniques second edition" (2008) written by Greg T. Hermanson, "Pegylated Protein Drug: basic Science and Clinical Application" (2009) written by Francesco M. Veronese, and the like.

The bio-related substance means a substance relating to a living body and indicates proteins having a physiological activity, enzymes, genes, nucleic acids, polypeptides, oligopeptides, amino acids, cytokines, hormones, antibodies, and derivatives thereof. Moreover, it includes drugs such as phospholipid derivatives and anticancer agents. Preferred examples of X and Y are not particularly limited as far as they are functional groups capable of chemically bonding to an amino group, a mercapto group, a carboxyl group, an aldehyde group, an unsaturated bond, or an azido group of the bio-related substances mentioned above.

Further specifically, there may be mentioned functional groups including a substituted active ester, an active carbonate, an aldehyde, an isocyanate, an isothiocyanate, an epoxide, a thiol, a substituted maleimide, a hydrazide, a dithiopyridine, a substituted sulfonate, an amine, an oxyamine, an α-haloacetyl, a carboxylic acid, a substituted unsaturated bond, an azide, and the like.

Furthermore, the functional group capable of reacting with an amino group of the bio-related substances is a substituted active ester, an active carbonate, an aldehyde, an isocyanate, an isothiocyanate, an epoxide, a substituted maleimide, a dithiopyridine, a substituted sulfonate, a carboxylic acid, or a substituted unsaturated bond; the functional group capable of reacting with a mercapto group of the bio-related substances is a substituted active ester, an active carbonate, an aldehyde, an isocyanate, an isothiocyanate, an epoxide, a thiol, a substituted maleimide, a dithiopyridine, a substituted sulfonate, an iodoacetamide, a carboxylic acid, or a substituted unsaturated bond; the functional group capable of reacting with a carboxyl group or an aldehyde group of the bio-related substances is a thiol, an amine, or an oxyamine; the functional group capable of reacting with an unsaturated bond of the bio-related substances is an amine, a thiol, or an azide; and the functional group capable of reacting with an azido group of the bio-related substances is an unsaturated bond.

In a preferred embodiment, X and Y are a group shown in Group (I), Group (II), Group (III), Group (IV), or Group (V).
Group (I): functional groups capable of reacting with an amino group of the bio-related substances
  the following (a), (b), (c), (d), (e), (f), (h), (i), (j)
Group (II): functional groups capable of reacting with a mercapto group of the bio-related substances
  the following (a), (b), (c), (d), (e), (f), (g), (h), (i), (j)
Group (III): functional groups capable of reacting with a carboxyl group or an aldehyde group of the bio-related substances
  the following (g), (k), (l), (m)

Group (IV): functional groups capable of reacting with an unsaturated bond of the bio-related substances
the following (g), (k), (m), (n)

Group (V): functional groups capable of reacting with an azido group of the bio-related substances
the following (j)

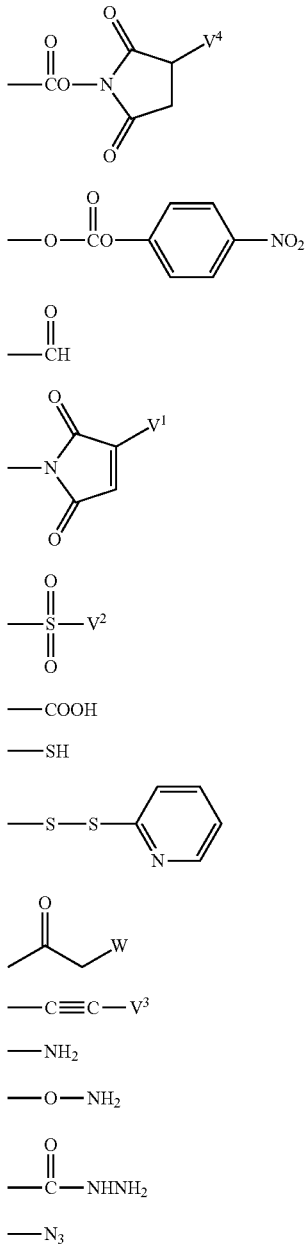

In the formula, $V^1$ and $V^3$ represent a hydrocarbon group having 1 to 5 carbon atoms. Specific hydrocarbon group includes a methyl group, an ethyl group, a propyl group, an isopropyl group, a butyl group, a tert-butyl group, and a pentyl group.

$V^2$ is a hydrocarbon group having 1 to 10 carbon atoms that may contain a halogen atom and specific hydrocarbon group having 1 to 10 carbon atoms that may contain a halogen atom includes saturated or unsaturated aliphatic hydrocarbon groups, aliphatic aromatic or aromatic hydrocarbon groups that may be substituted with a halogen atom, such as a methyl group, an ethyl group, a propyl group, an isopropyl group, a butyl group, a tert-butyl group, a pentyl group, an isopentyl group, a hexyl group, a benzyl group, a 4-methylphenyl group, a trifluoromethyl group, a 2,2,2-trifluoroethyl group, a 4-(trifluoromethoxy)phenyl group, a vinyl group, a chloroethyl group, a bromoethyl group, and an iodoethyl group, but preferred are a methyl group, a vinyl group, a 4-methylphenyl group, and a 2,2,2-trifluoroethyl group.

$V^4$ represents a hydrogen atom or a sulfonyl group and is preferably a hydrogen atom.

W is a halogen atom selected from Cl, Br, and I.

$L^1$ in the formulae (1) and (2) and $L^2$ in the formula (1) are a linker between the functional group X or Y and the polyoxyalkylene chain and $L^3$ in the formulae (1) and (2) is a linker between the hydroxyl group-removed residue of pentaerythritol or dipentaerythritol and the polyoxyalkylene chain. They are not particularly limited as far as they are a covalent bond and preferably include alkylene groups themselves or alkylene groups containing an ester bond, a urethane bond, an amide bond, an ether bond, a carbonate bond, or a secondary amino group. Preferred examples of the alkylene group include structures such as (z1). Preferred examples of the alkylene group containing an ether bond include structures such as (z2) and (z3). Preferred examples of the alkylene group containing an ester bond include structures such as (z4). Preferred examples of the alkylene group containing a urethane bond include structures such as (z5). Preferred examples of the alkylene group containing an amide bond include structures such as (z6). Preferred examples of the alkylene group containing a secondary amino group include structures such as (z7). In each formula, t is an integer of 0 to 12. A preferred range of t in (z2), (z4), (z5), or (z7) is 0 or 1 to 12. For example, in the case where bonding in a hydrophobic environment such as inside of a protein is intended, t is preferably larger and, in the case where bonding in a hydrophilic environment is intended, t is preferably smaller. A preferred range of t in (z1), (z3), or (z6) is 1 to 12 and t is selected depending on a bonding environment. t in (z6) or (z7) may be the same or different.

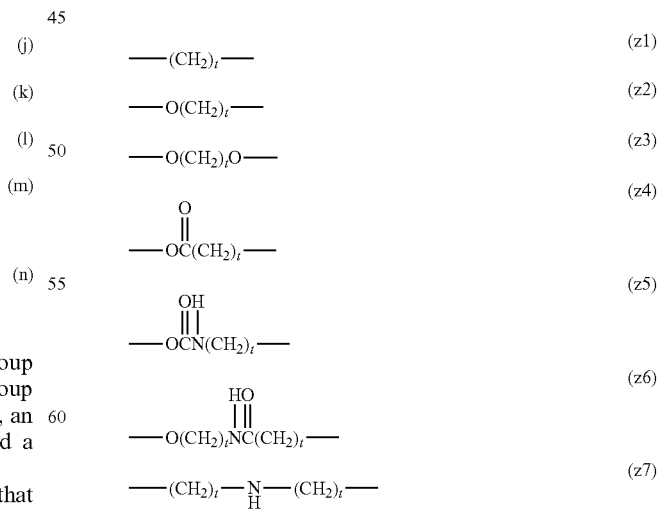

In the intermediate represented by the formula (2), $OA^1$, $OA^2$, $L^1$, $L^3$, m, n, p, r, $s^1$, and $s^2$ are the same as above.

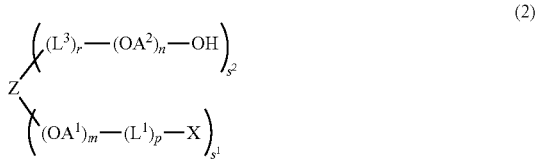
(2)

The branched hetero polyfunctional polyoxyalkylene compound represented by the formula (1) of the invention is produced by functionalizing the hydroxyl group of the compound (2) represented by the formula (2) into a group capable of a chemical reaction with a bio-related substance, which is different from X.

The polyoxyalkylene compound (2) can be, for example, produced as follows. In the case where Z is a hydroxyl group-removed residue of pentaerythritol, the compound can be produced as follows. 2,2-Dimethyl-5,5-bis(hydroxymethyl)-1,3-dioxane wherein only two hydroxyl groups undergo cyclic acetalization can be obtained by reacting pentaerythritol with 2,2-dimethoxypropane in an aprotic solvent in the presence of an acid catalyst. The reaction solvent is not particularly limited as far as it is an aprotic solvent but, since pentaerythritol is difficult to dissolve, a highly polar solvent such as N,N-dimethylformamide is preferred. The acid catalyst is not particularly limited but is preferably p-toluenesulfonic acid which is used in a general ketalization reaction. With regard to the charging molar ratio, 2,2-dimethoxypropane is charged in an amount of 0.8 to 1.2 moles, preferably equivalent mole relative to 1 mole of pentaerythritol. With regard to the charging method, pentaerythritol, the solvent, and the acid catalyst may be mixed and heated and 2,2-dimethoxypropane may be reacted in a homogeneous state or it may be reacted after pentaerythritol is dispersed as fine crystals into the solvent.

In the crude product after the reaction, there are impurities such as a compound wherein all four hydroxyl groups undergo cyclic acetalization and starting pentaerythritol, but the crude product can be purified by solid-liquid extraction, adsorbent, column chromatography, and/or the like. With regard to the solid-liquid extraction, the compound wherein all four hydroxyl groups have undergone cyclic acetalization can be removed by dispersing the crude product into a non-polar solvent in which the objective compound does not dissolve and washing the product therein. The non-polar solvent is not particularly limited as far as it is a solvent in which the objective compound does not dissolve but is preferably hexane or heptane. Moreover, by dissolving the crude product in a polar solvent, only the objective compound is dissolved and starting pentaerythritol can be filtrated off. The polar solvent is not particularly limited as far as it is a solvent in which pentaerythritol is insoluble but is preferably ethyl acetate. With regard to the solid-liquid extraction, a Soxhlet extractor may be used.

Moreover, the adsorbent is not particularly limited but an inorganic adsorbent having an interaction with a hydroxyl group is aluminum oxide, silicon dioxide, or a composite oxide composed of aluminum and silicon. Preferred specific examples include active alumina, silica gel, and Kyoward 200B and Kyoward 700 of Kyoward series manufactured by Kyowa Chemical Industry Co., Ltd. Furthermore, purification is also possible using column chromatography.

The objective compound wherein two hydroxyl groups are selectively protected can be obtained by the purification using the method(s) as mentioned above. However, when alkylene oxide addition and functionalization are performed in a state that the impurities remain in the starting material for the polymerization, low-molecular-weight reactive impurities and quadruple-chain reactive impurities are formed and these impurities remarkably lower purity and homogeneity of a polyoxyalkylene-modified compound as a final drug.

Thus, 2,2-dimethyl-5,5-bis(hydroxymethyl)-1,3-dioxane wherein two hydroxyl groups are selectively protected can be obtained. A protective group for two hydroxyl groups is not particularly limited but two hydroxyl groups may be simultaneously protected with an isopropylidene group or a benzylidene group or two hydroxyl groups may be selectively protected with a known protective group such as a benzyl group or a t-butyl group. The obtained starting material for the polymerization may be purified on a silica gel column or the like. An alkylene oxide is polymerized to remaining two hydroxyl groups in an amount of 5 to 1,000 moles and the terminal ends are subjected to functionalization. Then, the protective group is deprotected and the alkylene oxide is polymerized to the newly formed hydroxyl group in an amount of 0 to 1,000 moles, whereby the target compound can be obtained.

A reaction path of the compound (2) in the case where the protective group is an isopropylidene group is shown below.

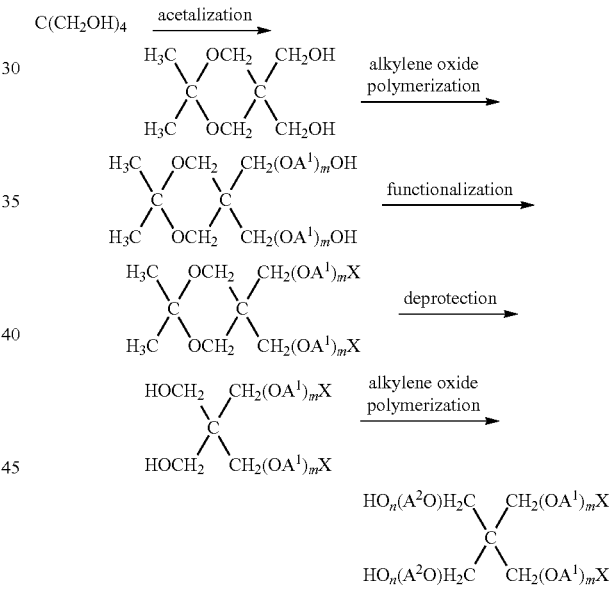

Moreover, the compound (2) can be also produced by the following method.

For example, an alkylene oxide is polymerized to a compound wherein two hydroxyl groups of pentaerythritol are simultaneously protected, such as 2,2-dimethyl-5,5-bis(hydroxymethyl)-1,3-dioxane, in an amount of 5 to 1,000 moles and the terminal ends are subjected to functionalization, followed by deprotection. After newly formed two hydroxyl groups are activated with a functional group such as p-nitrophenyl carbonate or an N-hydroxysuccinimidyl group, the groups are reacted with an aminopolyoxyalkylene compound wherein one terminal end is protected with a benzyl group, a t-Bu group, or the like and then the protective group such as the benzyl group or the t-Bu group is deprotected, whereby the compound of the formula (2) can be obtained.

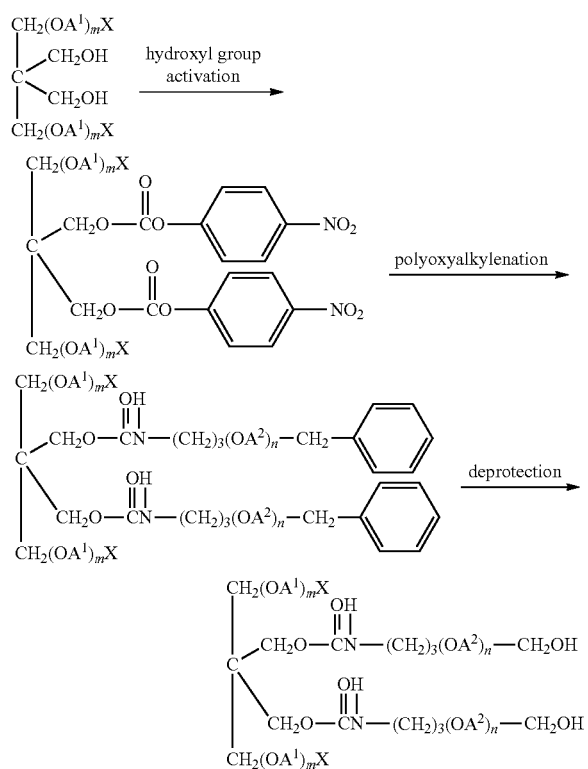
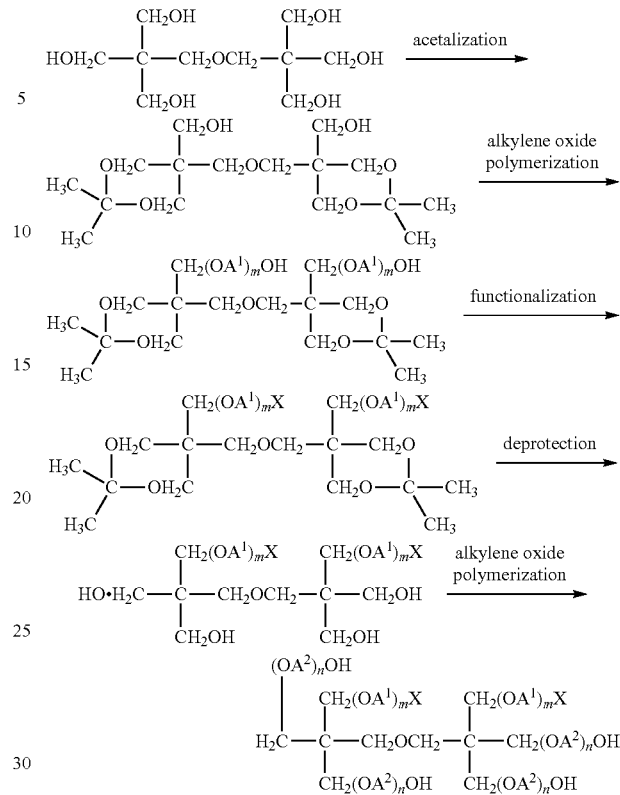

In the above, an example wherein Z is a hydroxyl group-removed residue of pentaerythritol is mentioned but, in the case where Z is a hydroxyl group-removed residue of dipentaerythritol, for example, the compound (2) having four hydroxyl groups can be obtained by the following method. The hydroxyl groups of dipentaerythritol are protected with protective groups such as two isopropylidene groups, an alkylene oxide is polymerized to remaining hydroxyl groups in an amount of 5 to 1,000 moles, and the terminal ends are subjected to functionalization. The isopropylidene groups are deprotected and an alkylene oxide is polymerized to newly formed four hydroxyl groups in an amount of 0 to 1,000 moles, whereby the compound (2) can be obtained.

Moreover, the following shows a method of synthesizing the compound (2) having two hydroxyl groups in the case where Z is a hydroxyl group-removed residue of dipentaerythritol. The hydroxyl groups of dipentaerythritol are protected with two isopropylidene groups or the like, an alkylene oxide is polymerized to remaining hydroxyl groups in an amount of 0 to 1,000 moles, and the terminal ends are protected with a hydroxyl group-protective group such as a benzyl group. The isopropylidene groups are deprotected, an alkylene oxide is polymerized to newly formed four hydroxyl groups in an amount of 5 to 1,000 moles, and the terminal ends are subjected to functionalization. Then, the compound (2) can be obtained by deprotecting the benzyl group.

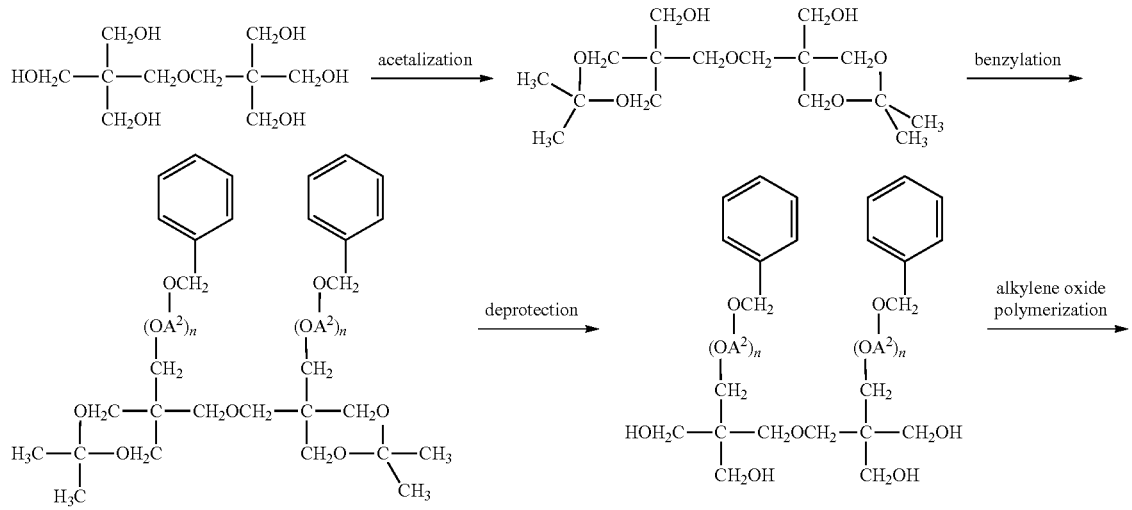

-continued

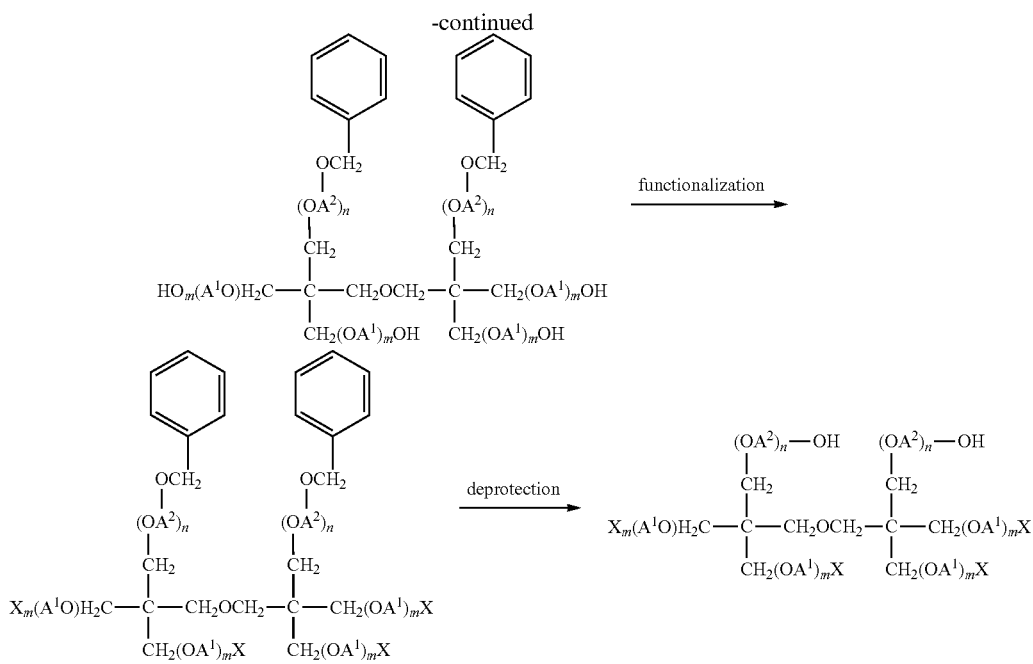

As above, contrary to the conventional art producing method wherein a polyoxyalkylene derivative prepared beforehand is reacted with a core skeleton compound, by using the alkylene oxide addition polymerization reaction as in the present invention, a highly pure branched hetero polyfunctional polyoxyalkylene compound can be produced by the high-yield and industrially suitable method.

The thus obtained compound of the formula (2) may be purified by a purification means such as extraction, recrystallization, adsorption treatment, reprecipitation, column chromatography, or supercritical extraction.

Then, by functionalizing the hydroxyl group of the thus obtained compound (2) into a group capable of a chemical reaction with a bio-related substance, which is different from X, the branched hetero polyfunctional polyoxyalkylene compound represented by the formula (1) of the invention can be produced.

The following describes methods for synthesizing the compounds having the functional groups (a) to (n) in detail.

With regard to the synthesis of (a) to (n), the compounds (1) of the invention can be also obtained by using the compounds having (a) to (n) themselves as intermediates and further reacting them with other compounds. For example, using an intermediate having a functional group (k) as a starting material, a functional group (a) or (d) can be obtained.

In the following description, "compound having the functional group (a) . . . " is sometimes referred to as "compound (a) . . . " or "(a) . . . body".

[Producing Method of Compound (b) or (e)]

(b) and (e) can be introduced respectively by reacting the compound (2) with an organic base such as triethylamine, pyridine, or 4-dimethylaminopyridine or an inorganic base such as sodium carbonate, sodium hydroxide, sodium hydrogen carbonate, sodium acetate, potassium carbonate, or potassium hydroxide and either of compounds represented by the following formulae (b1) and (e1) in an aprotic solvent such as toluene, benzene, xylene, acetonitrile, ethyl acetate, diethyl ether, t-butyl methyl ether, tetrahydrofuran, chloroform, methylene chloride, dimethyl sulfoxide, dimethylformamide, or dimethylacetamide or with no solvent. Moreover, the above organic base and inorganic base may not be used. The ratio of the organic base or inorganic base to be used is not particularly limited but is preferably equivalent mole or more relative to the compound (2). Furthermore, the organic base may be used as a solvent. $W^2$ in (b1) and (e1) is a halogen atom selected from Cl, Br, and I and is preferably Cl. The ratio of the compound represented by the general formula (b1) or (e1) to be used is not particularly limited but is preferably equivalent mole or more relative to the compound (2) and further preferably, it is preferred to carry out the reaction in the range of equivalent mole to 50 moles. The reaction temperature is preferably 0 to 300° C., further preferably 20 to 150° C. The reaction time is preferably 10 minutes to 48 hours, further preferably 30 minutes to 24 hours. The formed compounds may be purified by a purification means such as extraction, recrystallization, adsorption treatment, reprecipitation, column chromatography, or supercritical extraction.

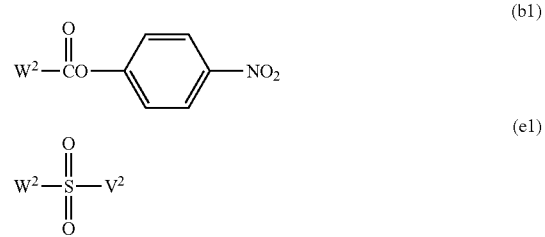

wherein $W^2$ represents a halogen atom selected from Cl, Br, and I and $V^2$ represents a hydrocarbon group having 1 to 10 carbon atoms in which a halogen atom may be used.

Also, (e) can be introduced by reacting the compound (2) with divinyl sulfone in an aprotic solvent such as toluene in the presence of a strong base. The strong base may be either an inorganic base or an organic base and is not particularly limited. The ratio of the strong base to be used is not particularly limited but is preferably equivalent mole or more relative to the compound (2). The ratio of the divinyl sulfone to be used is not particularly limited but is preferably equivalent mole or more relative to the compound (2) and, in order to prevent formation of a dimer as a by-product, it is preferred to use such an excess amount as 10 equivalents or more. The reaction temperature is preferably 0 to 100° C., further preferably 20 to 40° C. The reaction time is preferably 10 minutes to 48 hours, further preferably 30 minutes to 24 hours. The formed compound may be purified by a purification means such as extraction, recrystallization, adsorption treatment, reprecipitation, column chromatography, or supercritical extraction.

[Producing Method of Compound (f)]

The carboxyl body (f) can be obtained by reacting the compound (2) or the amine body (k) to be mentioned later with a dicarboxylic anhydride such as succinic anhydride or glutaric anhydride.

The reaction of the compound (2) or the amine body (k) with the dicarboxylic anhydride is carried out in an aforementioned aprotic solvent or with no solvent. The ratio of the dicarboxylic anhydride to be used is not particularly limited but is preferably equivalent mole or more, further preferably equivalent mole to 5 moles relative to the compound (2). The reaction temperature is preferably 0 to 200° C., further preferably 20 to 150° C. The reaction time is 10 minutes to 48 hours, further preferably 30 minutes to 12 hours. In the reaction, an organic base such as triethylamine, pyridine, or dimethylaminopyridine or an inorganic base such as sodium carbonate, sodium hydroxide, sodium hydrogen carbonate, sodium acetate, potassium carbonate, or potassium hydroxide may be used as a catalyst. The ratio of the catalyst to be used is preferably 0.1 to 50% by mass, further preferably 0.5 to 20% by mass relative to the compound (2). The thus formed carboxyl body (f) may be purified by a purification means such as extraction, recrystallization, adsorption treatment, reprecipitation, column chromatography, or supercritical extraction or may be used as it is in the case where it is used as a starting material of a condensation reaction.

With regard to the compound (f), the carboxyl body (f) can be obtained by reacting the compound (2) with a halogenated carboxylic acid alkyl ester such as ethyl 6-bromohexanoate or ethyl 7-bromoheptanoate. The etherification reaction of the compound (2) with the halogenated carboxylic acid alkyl ester is carried out in an aforementioned aprotic solvent or with no solvent. The ratio of the halogenated carboxylic acid alkyl ester to be used is not particularly limited but is preferably equivalent mole or more, further preferably equivalent mole to 30 moles relative to the compound (2). The reaction temperature is preferably 0 to 200° C., further preferably 20 to 150° C. The reaction time is 10 minutes to 48 hours, further preferably 30 minutes to 12 hours. In the reaction, an organic base such as triethylamine, pyridine, or dimethylaminopyridine or an inorganic base such as sodium carbonate, sodium hydroxide, sodium hydrogen carbonate, sodium acetate, potassium carbonate, or potassium hydroxide may be used as a catalyst. The ratio of the catalyst to be used is preferably 0.1 to 500% by mass, further preferably 0.5 to 300% by mass relative to the compound (2). After the etherification, hydrolysis of the ester is carried out by adding an aqueous solution of sodium hydroxide, potassium hydroxide, or the like in the case of using the organic base or by adding water in the case of using the inorganic base. The reaction temperature is preferably 0 to 100° C., further preferably 20 to 100° C. The reaction time is 10 minutes to 48 hours, further preferably 30 minutes to 12 hours. After the reaction, neutralization is performed with hydrochloric acid, sulfuric acid, or the like. The thus formed carboxyl body (f) may be purified by a purification means such as extraction, recrystallization, adsorption treatment, reprecipitation, column chromatography, or supercritical extraction or may be used as it is in the case where it is used as a starting material of a condensation reaction.

[Producing Method of Compound (a)]

A succinimide body of (a) can be obtained by subjecting the carboxyl body (f) to a condensation reaction with N-hydroxysuccinimide in the presence of a condensing agent such as DCC or EDC. The condensation reaction is similarly carried out in an aforementioned aprotic solvent or with no solvent. The condensing agent is not particularly limited but is preferably DCC. The ratio of DCC to be used is preferably equivalent mole or more, further preferably equivalent mole to 5 moles relative to the carboxyl body (f). The ratio of N-hydroxysuccinimide to be used is preferably equivalent mole or more, further preferably equivalent mole to 5 moles relative to the carboxyl body (f). The reaction temperature is preferably 0 to 100° C., further preferably 20 to 80° C. The reaction time is 10 minutes to 48 hours, further preferably 30 minutes to 12 hours. The formed compound may be purified by a purification means such as extraction, recrystallization, adsorption treatment, reprecipitation, column chromatography, or supercritical extraction.

Also, the succinimide body (a) can be obtained by reacting the compound (2) with N,N'-disuccinimidyl carbonate. The reaction is carried out in an aprotic solvent or with no solvent as in the above reaction. The ratio of N,N'-disuccinimidyl carbonate to be used is preferably equivalent mole or more, further preferably equivalent mole to 5 moles relative to the compound (2). The reaction temperature is preferably 0 to 100° C., further preferably 20 to 80° C. The reaction time is 10 minutes to 48 hours, further preferably 30 minutes to 12 hours. The formed compound may be purified by a purification means such as extraction, recrystallization, adsorption treatment, reprecipitation, column chromatography, or supercritical extraction.

[Producing Method of Compound (k)]

The amine body of (k) can be obtained by adding acrylonitrile or the like to the compound (2) in a solvent such as water or acetonitrile using an inorganic base such as sodium hydroxide or potassium hydroxide as a catalyst to obtain a nitrile body and then carrying out a hydrogenation reaction of the nitrile group under a nickel or palladium catalyst in an autoclave. The ratio of the inorganic base to be used when the nitrile body is obtained is not particularly limited but is preferably 0.01 to 50% by mass relative to the compound (2). The ratio of acrylonitrile or the like to be used is not particularly limited but is preferably 0.5 to 5 times by mass relative to the mass of the compound (2) and further preferably, it is preferred to carry out the reaction in the range of 1 to 4 times by mass. Also, acrylonitrile may be used as a solvent. The reaction temperature is preferably −50 to 100° C., further preferably −20 to 60° C. The reaction time is 10 minutes to 48 hours, further preferably 30 minutes to 24 hours. A reaction solvent in the subsequent hydrogenation reaction of the nitrile body is not particularly limited as far as it is a solvent which is not involved in the reaction but is preferably toluene. The ratio of the nickel or palladium catalyst to be used is not particularly limited but is 0.05 to 30% by mass, preferably 0.5 to 20% by mass relative to the nitrile body. The reaction temperature is preferably 20 to 200° C., further preferably 50 to 150° C. The reaction time is 10 minutes to 48 hours, further preferably 30 minutes to 24 hours. A hydrogen pressure is preferably 2 to 10 MPa, further preferably 3 to 8 MPa. Moreover, in order to prevent dimerization, ammonia may be added into the reaction system. An ammonia pressure in the case of adding ammonia is not particularly limited but is 0.1 to 10 MPa, further preferably 0.3 to 2 MPa. The formed compound may be purified by an aforementioned purification means.

Also, the above amine body (k) can be obtained by reacting the compound (e) with aqueous ammonia. The reaction is carried out in aqueous ammonia and the concentration of ammonia is not particularly limited but is preferably in the range of 10 to 40% by mass. The ratio of the aqueous ammonia to be used is preferably 1 to 300 times the mass of the compound (e). The reaction temperature is preferably 0 to 100° C., further preferably 20 to 80° C. The reaction time is preferably 10 minutes to 72 hours, further preferably 1 to 36 hours. Moreover, the amine body (k) can be also obtained by reacting the compound (e) with ammonia in an autoclave. A reaction solvent is not particularly limited but preferably includes methanol and ethanol. The amount of ammonia is preferably 10 to 300% by mass, further preferably 20 to 200% by mass relative to the compound (e). The reaction temperature is preferably 50 to 200° C., further preferably 80 to 150° C. The reaction time is preferably 10 minutes to 24 hours, further preferably 30 minutes to 12 hours. The formed compound may be purified by an aforementioned purification means.

Also, the amine body (k) can be obtained by bonding the compound (2) to phthalimide in an aprotic solvent by Mitsunobu reaction, followed by deprotection with a polyfunctional amine. The reaction conditions for Mitsunobu reaction are not particularly limited but chloroform or dichloromethane is preferred as the reaction solvent. Moreover, it is preferred to use triphenylphosphine in an amount of equivalent mole or more, preferably equivalent mole to 50 moles relative to the compound (2) and diisopropyl azodicarboxylate in an amount of equivalent mole or more, preferably equivalent mole to 50 moles relative to the compound (2). The reaction temperature is preferably 0 to 100° C., further preferably 10 to 50° C. The reaction time is preferably 10 minutes to 72 hours, further preferably 30 minutes to 6 hours.

For deprotection, a polyfunctional amine such as hydrazine or ethylenediamine is preferably used in an amount of equivalent mole or more, preferably equivalent mole to 500 moles relative to the compound (2). A reaction solvent is not particularly limited but methanol is preferred. The reaction temperature is preferably 0 to 100° C., further preferably 20 to 80° C. The reaction time is preferably 10 minutes to 72 hours, further preferably 1 to 10 hours. The formed compound may be purified by a purification means such as extraction, recrystallization, adsorption treatment, reprecipitation, column chromatography, or supercritical extraction.

[Producing Method of Compound (l)]

The phthalimide body (12) can be obtained by reacting the carbonate body (b) with the compound (11) in the presence of an alkali catalyst such as triethylamine or pyridine. A reaction solvent is not particularly limited as far as it is no solvent or a polar solvent but is preferably methanol. The ratio of the alkali catalyst to be used is not particularly limited but is preferably equivalent mole or more relative to the carbonate body (b) and further preferably, it is more preferred to carry out the reaction in the range of equivalent mole to 20 moles. The ratio of the compound (11) to be used is preferably equivalent mole or more, further preferably equivalent mole to 20 moles relative to the carbonate body (b). The reaction temperature is preferably 0 to 100° C., further preferably 20 to 80° C. The reaction time is preferably 10 minutes to 48 hours, further preferably 30 minutes to 12 hours. The formed compound may be purified by a purification means such as extraction, recrystallization, adsorption treatment, reprecipitation, column chromatography, or supercritical extraction or may be used in the next step without purification.

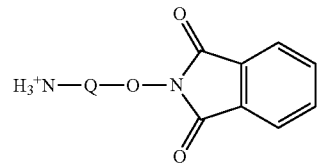

(ll)

wherein Q represents an alkylene group having 1 to 7 carbon atoms.

The oxyamine body (1) can be obtained by reacting the phthalimide body (12) in the presence of a polyfunctional amine such as hydrazine or ethylenediamine.

A reaction solvent is not particularly limited but is preferably N,N-dimethylformamide or methylene chloride. The ratio in the presence of the polyfunctional amine to be used is not particularly limited but is preferably equivalent mole or more relative to the compound (12) and further preferably, it is more preferred to carry out the reaction in the range of equivalent mole to 50 moles. The reaction temperature is preferably 0 to 100° C., further preferably 20 to 80° C. The reaction time is preferably 10 minutes to 48 hours, further preferably 30 minutes to 12 hours. The formed compound may be purified by a purification means such as extraction, recrystallization, adsorption treatment, reprecipitation, column chromatography, or supercritical extraction.

[Producing Method of Compound (d)]

The maleimide body of (d) can be obtained by reacting the amine body (k) obtained by the aforementioned method with maleic anhydride in an aforementioned aprotic solvent or with no solvent to obtain a maleamide body and subsequently subjecting the maleamide body to a ring-closure reaction using acetic anhydride and sodium acetate as a catalyst. The ratio of the maleic anhydride to be used in the maleamide-forming reaction is not particularly limited but is preferably equivalent mole or more, further preferably equivalent mole to 5 moles relative to the amine body (k). The reaction temperature is preferably 0 to 200° C., further preferably 20 to 120° C. The reaction time is preferably 10 minutes to 48 hours, further preferably 30 minutes to 12 hours. The formed maleamide body may be purified by an aforementioned purification means or may be used as it is in the next ring-closure reaction.

A reaction solvent in the subsequent ring-closure reaction is not particularly limited but is preferably an aprotic solvent or acetic anhydride. The ratio of sodium acetate to be used is not particularly limited but is preferably equivalent mole or more, further preferably equivalent mole to 50 moles relative to the maleamide body. The reaction temperature is preferably 0 to 200° C., further preferably 20 to 150° C. The reaction time is preferably 10 minutes to 48 hours, further preferably 30 minutes to 12 hours. The formed compound may be purified by an aforementioned purification means.

The above maleimide body can be obtained by reacting the following general formula (d1) with the aforementioned amine body of (k). The reaction is carried out in an aforementioned aprotic solvent or with no solvent and the compound (d1) is added in an amount of equivalent mole or more relative to the amine body of (k) and reacted. The ratio of (d1) to be used is preferably equivalent mole or more, further preferably equivalent mole to 5 moles relative to the amine body (k). The reaction temperature is preferably 0 to 200° C., further preferably 20 to 80° C. The reaction time is preferably 10 minutes to 48 hours, further preferably 30 minutes to 12 hours. At the reaction, light shielding may be performed. The formed compound may be purified by an aforementioned purification means.

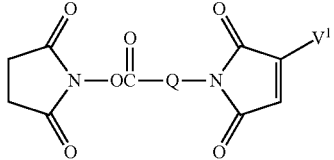

(d1)

wherein Q represents an alkylene group having 1 to 7 carbon atoms and $V^1$ represents a hydrocarbon having 1 to 5 carbon atoms.

[Producing Method of Compound (c)]

The aldehyde body (c) can be obtained by reacting the compound (e) with an acetal compound of (c1) to obtain an acetal body and then hydrolyzing it under acidic conditions. The acetalization reaction can be attained by reacting (c1) in an amount of preferably equivalent mole or more, preferably equivalent mole to 50 moles relative to the compound (e) in an aforementioned aprotic solvent or in no solvent. (c1) can be prepared from the corresponding alcohol using metal sodium, metal potassium, sodium hydride, potassium hydride, sodium methoxide, potassium t-butoxide, or the like. The reaction temperature is preferably 0 to 300° C., further preferably 20 to 150° C. The reaction time is preferably 10 minutes to 48 hours, further preferably 30 minutes to 24 hours.

In the case of using (c2), after the hydroxyl group of the compound (2) is converted into an alcoholate by the aforementioned method, the acetal body can be obtained by reacting (c2) in a ratio of equivalent mole or more, preferably equivalent mole to 100 moles in an aforementioned aprotic solvent or with no solvent. The reaction temperature is preferably 0 to 300° C., further preferably 20 to 150° C. The reaction time is preferably 10 minutes to 48 hours, further preferably 30 minutes to 24 hours.

In the case of using (c3), the acetal body can be obtained by reacting the compound (a), (b), (e), or (f) with (c3). The production of the compound (a), (b), (e), or (f) is as mentioned above. In the reaction with (c3), a solvent is not particularly limited but the reaction is carried out in an aforementioned aprotic solvent. The ratio of (c3) to be charged relative to the compound (a), (b), (e), or (f) is preferably equivalent mole or more, further preferably equivalent mole to 10 moles. The reaction temperature is preferably −30 to 200° C., further preferably 0 to 150° C. The reaction time is preferably 10 minutes to 48 hours, further preferably 30 minutes to 24 hours. In the case of using (f), a condensing agent such as DCC or EDC may be appropriately used. All the acetalization reactions may be carried out with light shielding. The thus obtained acetal body may be purified by an aforementioned purification means or may be used in the next aldehyde-forming reaction as it is without purification.

In aldehyde formation, an aldehyde can be produced by transforming the acetal body into a 0.1 to 50% aqueous solution and hydrolyzing it in an aqueous solution adjusted to pH 1 to 4 with an acid such as acetic acid, phosphoric acid, sulfuric acid, or hydrochloric acid. The reaction temperature is preferably −20 to 100° C., further preferably 0 to 80° C. The reaction time is preferably 10 minutes to 24 hours, further preferably 30 minutes to 10 hours. The reaction may be carried out with light shielding. The formed compound may be purified by an aforementioned purification means.

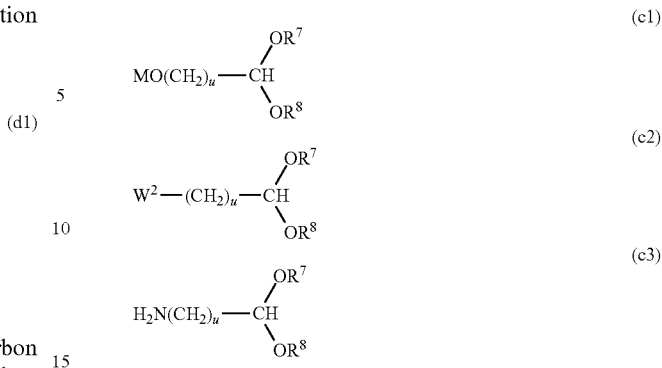

wherein $R^7$ and $R^8$ are a hydrocarbon group having 1 to 3 carbon atoms and may be the same or different from each other, and they may form a ring each other; M is sodium or potassium; $W^2$ is a halogen atom selected from Cl, Br, and I; and u is an integer of 1 to 5.

[Producing Method of Compound (g)]

The mercapto body (g) can be obtained by reacting the compound (e) with a thiation agent such as thiourea. The production of the compound (e) is as mentioned above. The thiation reaction is carried out in a solvent such as water, an alcohol, or acetonitrile or with no solvent. The ratio of thiourea to be used is preferably equivalent mole or more, further preferably in the range of equivalent mole to 50 moles relative to the compound (e). The reaction temperature is preferably 0 to 300° C., further preferably 20 to 150° C. The reaction time is preferably 10 minutes to 48 hours, further preferably 30 minutes to 24 hours. After the reaction, the formed isothiouronium salt is subjected to alkaline hydrolysis, whereby the mercapto body can be obtained. The formed compound may be purified by an aforementioned purification means.

Also, the above mercapto body (g) can be obtained by reacting the compound (e) with the following compound (g1), followed by decomposition with a primary amine. The reaction of (e) with (g1) is carried out in an aforementioned aprotic solvent or with no solvent. The ratio of (g1) to be used is preferably equivalent mole or more, further preferably in the range of equivalent mole to 50 moles relative to the compound (e). The reaction temperature is preferably 0 to 300° C., further preferably 20 to 80° C. The reaction time is preferably 10 minutes to 48 hours, further preferably 30 minutes to 24 hours. Subsequent alkaline decomposition with a primary amine is carried out in an aforementioned aprotic solvent or with no solvent. The primary amine to be used is not particularly limited but preferably includes ammonia, methylamine, ethylamine, propylamine, butylamine, pentylamine, hexylamine, cyclohexylamine, ethanolamine, propanolamine, butanolamine, and the like. As a matter of course, these primary amines may be used as solvents. The formed compound may be purified by an aforementioned purification means.

(g1)

[Producing Method of Compound (h)]

The compound (h) can be obtained by reacting the mercapto body (g) with 2,2'-dipyridyl disulfide. In the reaction, a solvent is not particularly limited but the reaction is preferably carried out in an alcohol solvent. The ratio of 2,2'-dipyridyl disulfide to be charged relative to the mercapto body (g) is preferably equivalent mole or more, further preferably equivalent mole to 50 moles. The reaction temperature is preferably −30 to 100° C., further preferably 0 to 60° C. The reaction time is preferably 10 minutes to 48 hours, further preferably 30 minutes to 24 hours. The thus obtained disulfide body may be purified by an aforementioned purification means.

[Producing Method of Compound (i)]

The compound (i) can be obtained by reacting the amine body (k) obtained by the method as mentioned above with iodoacetic anhydride in an aforementioned aprotic solvent or with no solvent. The ratio of iodoacetic anhydride to be used is not particularly limited but is preferably equivalent mole or more, further preferably equivalent mole to 5 moles relative to the compound (k). The reaction temperature is preferably 0 to 200° C., further preferably 20 to 120° C. The reaction time is preferably 10 minutes to 48 hours, further preferably 30 minutes to 12 hours. The formed compound (i) may be purified by a purification means such as extraction, recrystallization, adsorption treatment, reprecipitation, column chromatography, or supercritical extraction.

Also, the compound (i) can be obtained by subjecting the amine body (k) to a condensation reaction with iodoacetic acid in the presence of a condensing agent such as DCC or EDC. The condensation reaction is similarly carried out in an aforementioned aprotic solvent or with no solvent. The condensing agent is not particularly limited but is preferably DCC. The ratio of DCC to be used is preferably equivalent mole or more, further preferably equivalent mole to 5 moles relative to the compound (k). The ratio of iodoacetic acid to be used is preferably equivalent mole or more, further preferably equivalent mole to 5 moles relative to the compound (k). The reaction temperature is preferably 0 to 100° C., further preferably 20 to 80° C. The reaction time is 10 minutes to 48 hours, further preferably 30 minutes to 12 hours. The formed compound may be purified by an aforementioned purification means.

[Producing Method of Compound (m)]

The compound (m) can be obtained by reacting the compound (a), (b), (c), or (e) with tert-butyl carbazinate in an aforementioned aprotic solvent or with no solvent and deprotecting the tert-butoxycarbonyl group. The ratio of tert-butyl carbazinate to be used is not particularly limited but is preferably equivalent mole or more, further preferably equivalent mole to 10 moles relative to the compound (a). The reaction temperature is preferably 0 to 200° C., further preferably 20 to 80° C. The reaction time is preferably 10 minutes to 48 hours, further preferably 30 minutes to 12 hours. The formed compound (m) may be purified by an aforementioned purification means.

[Producing Method of Compound (j)]

The acetylene compound (j) can be obtained by reacting the compound (a), (b), (c), or (e) with an acetylene compound represented by (j1). The production of the compound (a), (b), (c), or (e) is as mentioned above. The acetylene-forming reaction can be attained by reacting equivalent mole or more, preferably equivalent mole to 50 moles of (j1) relative to the compound (a), (b), (c), or (e) in a protic solvent or with no solvent. The reaction temperature is preferably 0 to 300° C., further preferably 20 to 150° C. The reaction time is preferably 10 minutes to 48 hours, further preferably 30 minutes to 24 hours. The formed compound may be purified by an aforementioned purification means.

$$NH_2—(CH_2)_u—C≡C—V^3 \quad (j1)$$

wherein u is an integer of 1 to 5 and $V^3$ represents a hydrocarbon group having 1 to 5 carbon atoms.

[Producing Method of Compound (n)]

An azide compound (n) can be obtained by reacting the compound (e) with sodium azide. The azide-forming reaction can be attained by reacting the compound (e) with equivalent mole or more, preferably equivalent mole to 50 moles of sodium azide in a protic solvent or with no solvent. The reaction temperature is preferably 0 to 300° C., further preferably 20 to 150° C. The reaction time is preferably 10 minutes to 48 hours, further preferably 30 minutes to 24 hours. The formed compound may be purified by an aforementioned purification means.

EXAMPLES

The present invention will be illustrated in greater detail with reference to the following Examples, but the invention should not be construed as being limited thereto. Incidentally, for analysis and identification of the compounds in examples, $^1$H-NMR and TOF-MS were used.

<Analytical Method of $^1$H-NMR>

In $^1$H-NMR analysis, JNM-ECP400 and JNM-ECA600 manufactured by Nippon Denshi Datum K. K. were employed. As integral values in the NMR measurement, theoretical values were described.

<Analytical Method of TOF-MS>

For measurement of molecular weight, measurement was performed by means of TOF-MS (autoflex III manufactured by Bruker) using Dithranol as a matrix and sodium trifluoroacetate as a salt. For analysis, analysis of molecular weight distribution was performed on Polytools using FlexAnalysis. Barycentric values obtained were described as values of molecular weight.

Example 1

Synthesis of compound (2) (case of Z=hydroxyl group-removed residue of pentaerythritol, $OA^1$=oxyethylene group, $OA^2$=oxyethylene group, n=1, $s^1$=2, $s^2$=2, p=0, r=0, X=amino group, molecular weight=about 2,000, 20,000)

Example 1-1

Into a 5 L round-bottom flask fitted with a thermometer, a nitrogen-introducing tube, and a stirrer were charged 254 g of pentaerythritol and 2,500 g of N,N-dimethylformamide, and they were heated and dissolved at 80° C. After cooling to 25° C., 195 g of 2,2-dimethoxypropane and 3.6 g of p-toluenesulfonic acid monohydrate were placed therein and, with introduction of nitrogen thereinto, a reaction was carried out at 25° C. without further treatment. Neutralization was performed by adding 9.5 g of triethylamine and the reaction solution was concentrated. After concentration, the resulting powder was dispersed in 1 kg of hexane, followed by stirring and filtration. The hexane-washing step was repeated four times. The resulting cake was dissolved in 1 kg of ethyl acetate at 50° C. and, after insoluble matter was filtrated, 250 g of Kyoward 200B was added to the filtrate and adsorption treatment was performed at 50° C. for 1 hour. The filtrate was concentrated to obtain 2,2-dimethyl-5,5-bis(hydroxymethyl)-1,3-dioxane.

$^1$H-NMR (D$_2$O, internal standard H$_2$O=4.65 ppm) δ(ppm): 1.40 (6H, s, —C$\underline{H}_3$), 2.69, 3.64 (4H, 4H, s, s, —C—C$\underline{H}_2$—C—, —C$\underline{H}_2$OH)

Example 1-2

Into a 5 L round-bottom flask fitted with a thermometer, a nitrogen-introducing tube, and a stirrer were charged 150 g of 2,2-dimethyl-5,5-bis(hydroxymethyl)-1,3-dioxane obtained in Example 1-1, 2,250 g of anhydrous N,N-dimethylformamide, and 22.0 g of tetrabutylammonium bromide, and they were dissolved at room temperature. After 588 g of 2-benzyloxyethyl methanesulfonate was charged therein, 111 g of sodium hydride was gradually added and a reaction was carried out at 50° C. After the reaction was quenched with 55 g of ethanol, 2,250 g of ion-exchange water, 2,250 g of ethyl acetate, and 2,250 g of hexane were added thereto and the whole was allowed to stand, followed by separation of an organic layer as an upper layer. After 3,000 g of ion-exchange water was added thereto, the whole was stirred and allowed to stand and an organic layer as an upper layer was separated. Then, 75 g of anhydrous magnesium sulfate was charged thereinto to dry the layer. After the organic layer was filtrated, the layer was concentrated under reduced pressure.

After 100 g of the resulting residue was dissolved in 1,500 g of tetrahydrofuran, 1,375 g of ion-exchange water and 125 g of conc. hydrochloric acid were added and a reaction was carried out at room temperature. After neutralized with 252 g of a 20% aqueous sodium hydroxide solution, the mixture was concentrated under reduced pressure. After 200 g of ethyl acetate was added thereto, the whole was stirred and allowed to stand. Subsequently, an organic layer as an upper layer was separated and 30 g of anhydrous magnesium sulfate was charged thereinto to dry the layer. After the organic layer was filtrated, the layer was concentrated under reduced pressure. Then, 40 g of hexane was added to the resulting residue, the whole was stirred and allowed to stand, and a hexane layer as an upper layer was removed.

After the reaction was carried out according to these steps using 520 g of the compound obtained in Example 1-1 in total, the resulting residue was purified by silica gel column chromatography (wako gel-C200, hexane/ethyl acetate=3/1→0/1) to obtain 2,2-bis{2-(benzyloxy)ethoxymethyl}-1,3-propanediol.

$^1$H-NMR (CDCl$_3$, internal standard TMS=0.00 ppm) δ(ppm): 2.95 (2H, t, —CH$_2$OH̲), 3.50-3.70 (16H, m, —CH̲$_2$OH, —CH$_2$O—CH$_2$CH$_2$—OBn), 4.05 (4H, s, —OCH̲$_2$Ph), 7.20-7.40 (5H, m, —OCH$_2$C$_6$H̲$_5$)

Example 1-3

Into a 100 L reaction autoclave were charged 0.73 kg of 2,2-bis{2-(benzyloxy)ethoxymethyl}-1,3-propanediol obtained in Example 1-2, 15.1 g of a 28% methanol solution of sodium methoxide, and 11 kg of anhydrous toluene, and inside of the system was subjected to substitution with nitrogen. After temperature was elevated to 50° C., the pressure was gradually reduced with maintaining the temperature and methanol and toluene were removed by distillation with introducing nitrogen thereinto. After the removal by distillation was continued for 1 hour, inside of the system was again subjected to substitution with nitrogen, temperature was elevated to 100° C., and 1.1 kg of ethylene oxide was added thereto at 100 to 150° C. under a pressure of 1 MPa or less, followed by continuation of the reaction for another 1 hour. After unreacted ethylene oxide gas was removed under reduced pressure, the whole was cooled to 40° C. and 57.5 g of a 28% methanol solution of sodium methoxide and 40 kg of anhydrous toluene were charged into the 100 L reaction autoclave and the inside of the system was subjected to nitrogen substitution. After the temperature was elevated to 105° C., methanol and toluene were removed by distillation with introducing nitrogen thereinto. After the removal by distillation was continued for 1 hour, inside of the system was again subjected to substitution with nitrogen, temperature was elevated to 100° C. and 1.5 kg of ethylene oxide was added thereto at 100 to 150° C. under a pressure of 1 MPa or less, followed by continuation of the reaction for another 5 hours. Then, 10 kg was taken out from the autoclave to obtain the following compound (p1).

$^1$H-NMR (CDCl$_3$, internal standard TMS) δ(ppm): 3.44-3.48 (8H, m, C—(CH̲$_2$)$_4$), 3.50-3.80 (136H, m, —(CH̲$_2$CH̲$_2$O)$_m$—H, —O—CH̲$_2$CH$_2$OBn), 4.55 (4H, s, —OCH̲$_2$Ph), 7.20-7.35 (10H, m, —OCH$_2$C$_6$H̲$_5$) TOF-MS analytical value (barycentric value of molecular weight): 1828

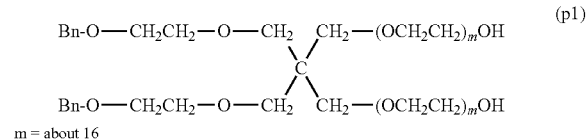

m = about 16

Example 1-4

In Example 1-3, about 23 kg of the reaction solution remaining in the autoclave was heated to 120° C. and 21.0 kg of ethylene oxide was introduced with a pressure of 1 MPa or less at 100 to 150° C., followed by the reaction for another 7 hours. After completion of the reaction, the whole was cooled to 70° C. and the following compound (p2) was obtained.

$^1$H-NMR (CDCl$_3$, internal standard TMS) δ(ppm): 2.74 (2H, t, —(CH$_2$CH$_2$O)$_m$—H̲), 3.44-3.48 (8H, m, C—(CH̲$_2$)$_4$), 3.50-3.80 (1792H, m, —(CH̲$_2$CH̲$_2$O)$_m$—H, —OCH̲$_2$CH̲$_2$OBn), 4.55 (4H, s, —OCH̲$_2$Ph), 7.20-7.35 (10H, m, —OCH$_2$C$_6$H̲$_5$) TOF-MS analytical value (barycentric value of molecular weight): 20045

$$\begin{array}{c} \text{Bn-O—CH}_2\text{CH}_2\text{—O—CH}_2 \quad \text{CH}_2\text{—(OCH}_2\text{CH}_2)_m\text{OH} \\ \diagdown \diagup \\ \text{C} \\ \diagup \diagdown \\ \text{Bn-O—CH}_2\text{CH}_2\text{—O—CH}_2 \quad \text{CH}_2\text{—(OCH}_2\text{CH}_2)_m\text{OH} \end{array} \quad (p2)$$

m = about 223

Example 1-5

Into a 500 mL round-bottom flask fitted with a thermometer, a nitrogen-introducing tube, a stirrer, a Dean-stark tube, and a condenser tube were charged 90 g of the compound of the formula (p2) and 159 g of toluene, and the whole was heated under reflux to remove 80 g of toluene and water as an azeotrope. After cooling to room temperature, 265 g of dichloromethane, 2.3 g of phthalimide, 4.2 g of triphenylphosphine, and 3.2 g of diisopropyl azodicarboxylate were charged thereinto successively, followed by a reaction at room temperature for 1 hour. After the reaction was quenched with methanol, concentration was performed under reduced pressure. Crystallization was effected by adding 318 g of ethyl acetate and 159 g of hexane to the concentrated solution. Crystals were collected by filtration and dried to obtain the following compound (p3).

$^1$H-NMR (CDCl$_3$, internal standard TMS) δ(ppm): 3.44-3.48 (8H, m, C—(CH̲$_2$)$_4$), 3.50-3.80 (1788H, m, —(CH̲$_2$CH̲$_2$O)$_m$—, —OCH̲$_2$CH̲$_2$OBn), 3.90 (4H, t, —OCH$_2$CH̲$_2$NPhth), 4.55 (4H, s, —OCH̲$_2$Ph), 7.20-7.35 (10H, m, —OCH$_2$C$_6$H̲$_5$), 7.72 (4H, dd, Ar—H̲), 7.85 (4H, dd, Ar—H̲)

(p3)

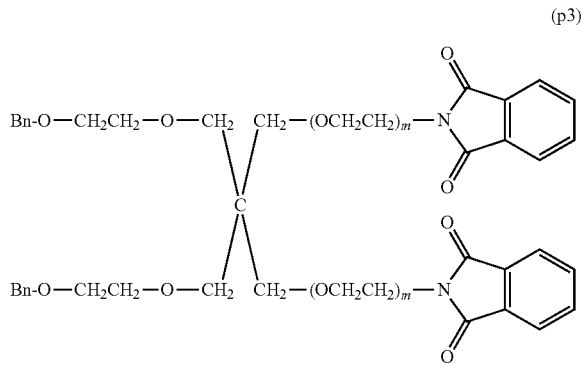

m = about 223

Example 1-6

Into a 1 L round-bottom flask fitted with a thermometer, a nitrogen-introducing tube, a stirrer, and a condenser tube were charged 45 g of the compound of the formula (p3) and 23 g of 5% Pd-carbon, followed by substitution with nitrogen. Then, 450 mL of methanol and 61 mL of cyclohexene were added, followed by a reaction at 55° C. for 6 hours. After cooling to 30° C., the catalyst was removed by filtration. The filtration cake was washed with 360 g of chloroform and, after 45 mg of 2,6-bis(1,1-dimethylethyl)-4-methylphenol was added, concentration was performed under reduced pressure. Then, 315 g of toluene and 23 g of anhydrous magnesium sulfate were charged into the residue to dry the organic layer. After the organic layer was filtered, 225 g of hexane was added to the filtrate to effect crystallization. The resulting crystals were collected by filtration and dried to obtain the following compound (p4).

$^1$H-NMR (CDCl$_3$, internal standard TMS) δ(ppm): 2.97 (2H, t, —(CH$_2$CH$_2$O)$_m$—$\underline{H}$), 3.44-3.48 (8H, m, C—(C$\underline{H}_2$)$_4$), 3.50-3.80 (1788H, m, —(C$\underline{H}_2$C$\underline{H}_2$O)$_m$—, —OC$\underline{H}_2$C$\underline{H}_2$OH), 3.90 (4H, t, —OCH$_2$C$\underline{H}_2$NPhth), 7.72 (4H, dd, Ar—$\underline{H}$), 7.85 (4H, dd, Ar—$\underline{H}$)

(p4)

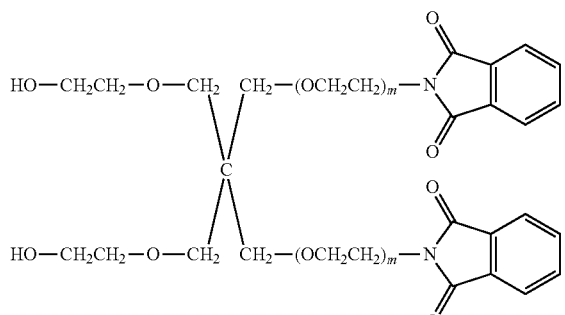

m = about 223

Example 1-7

Into a 300 mL round-bottom flask fitted with a thermometer, a nitrogen-introducing tube, a stirrer, and a condenser tube were charged 35 g of the compound of the formula (p4), 123 g of methanol, and 14 g of ethylenediamine monohydrate successively, followed by a reaction at 40° C. for 6 hours. After completion of the reaction, 175 g of ion-exchange water and 44 g of sodium chloride were successively added, then 350 g of dichloromethane was added thereto, and the whole was stirred and allowed to stand, followed by separation of a dichloromethane layer. After 11 g of anhydrous sodium sulfate was charged into the dichloromethane solution to dry the organic layer, the dichloromethane solution was filtrated and concentrated to about 70 mL. Then, 280 g of ethyl acetate and 140 g of hexane were added thereto to effect crystallization and crystals were collected by filtration and dried to obtain the following compound (p5).

$^1$H-NMR (CDCl$_3$, internal standard TMS) δ(ppm): 2.84 (4H, t, —OCH$_2$C$\underline{H}_2$NH$_2$), 3.44-3.48 (8H, m, C—(C$\underline{H}_2$)$_4$), 3.50-3.80 (1788H, m, —(C$\underline{H}_2$C$\underline{H}_2$O)$_m$—, —OC$\underline{H}_2$C$\underline{H}_2$OH)

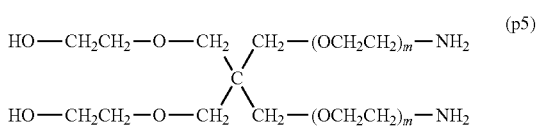

m = about 223

Example 2

Synthesis of compound (1) (case of Z=hydroxyl group-removed residue of pentaerythritol, OA$^1$=oxyethylene group, OA$^2$=oxyethylene group, n=0, s$^1$=2, s$^2$=2, p=1, q=1, r=0, L$^1$=alkylene group containing amide bond (z6 and t=2), L$^2$=alkylene group containing ether bond (z3 and t=2), X=maleimido group (functional group (d) and V$^1$=hydrogen), Y=succinimidyl carbonate group (functional group (a) and V$^4$=hydrogen), molecular weight=about 20,000)

Example 2-1

Into a 100 mL round-bottom flask fitted with a thermometer, a nitrogen-introducing tube, and a stirrer were charged 5 g of the compound of the formula (p5) and 30 g of acetonitrile, and they were dissolved. Then, 0.16 g of 3-maleimidopropionic succinimide was charged into the reaction vessel, followed by a reaction at room temperature for 3 hours. After the reaction solution was filtered and the filtrate was concentrated to about 10 mL, 50 g of ethyl acetate and 25 g of hexane were added to the concentrated solution to effect crystallization. Crystals were collected by filtration and dried to obtain the following compound (p6).

$^1$H-NMR (CDCl$_3$, internal standard TMS) δ(ppm): 2.51 (4H, t, C(O)C$\underline{H}_2$CH$_2$N<), 2.96 (2H, t, —CH$_2$C$\underline{H}_2$OH), 3.42 (4H, q, —C$\underline{H}_2$NHC(O)—), 3.44-3.48 (8H, m, C—(C$\underline{H}_2$)$_4$), 3.50-3.80 (1788H, m, —(C$\underline{H}_2$C$\underline{H}_2$O)$_m$—, —OC$\underline{H}_2$C$\underline{H}_2$OH), 3.84 (4H, t, C(O)CH$_2$C$\underline{H}_2$N<), 6.40 (2H, m, —N$\underline{H}$CO—), 6.70 (4H, s, —C$\underline{H}$=C$\underline{H}$—)

(p6)

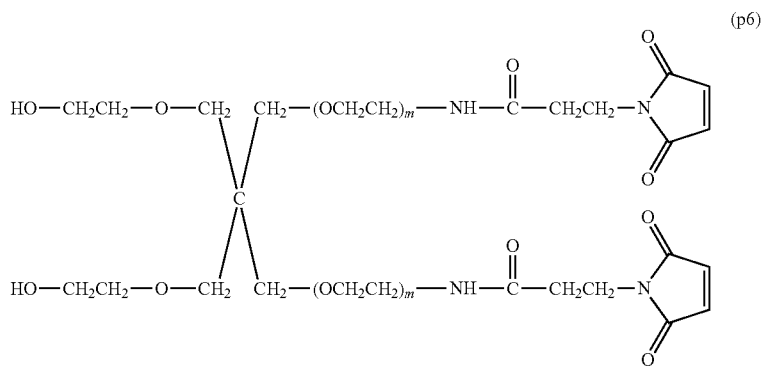

m = about 223

Example 2-2

Into a 100 mL round-bottom flask fitted with a thermometer, a nitrogen-introducing tube, and a stirrer were charged 3.5 g of the compound of the formula (p6) and 17.5 g of dichloromethane, and they were dissolved. Then, 0.6 g of disuccinimidyl carbonate and 0.1 g of triethylamine were charged into the reaction vessel, followed by a reaction at room temperature for 24 hours. After the reaction solution was filtrated and the filtrate was concentrated to about 10 mL, 70 g of ethyl acetate and 35 g of hexane were added to the concentrated solution to effect crystallization. Crystals were collected by filtration and dried to obtain the following compound (p7).

$^1$H-NMR (CDCl$_3$, internal standard TMS) δ(ppm): 2.52 (4H, t, C(O)C$\underline{H}_2$CH$_2$N<) 2.84 (8H, s, —OC(O)O$\underline{Su}$) 3.40-3.48 (12H, m, —C$\underline{H}_2$NHO(O)—, C—(C$\underline{H}_2$)$_4$) 3.50-3.80 (1784H, m, —(C$\underline{H}_2$C$\underline{H}_2$O)$_m$—, —OC$\underline{H}_2$CH$_2$OC(O)Su), 3.84 (4H, t, C(O)CH$_2$C$\underline{H}_2$N<), 4.44 (4H, m, —OCH$_2$C$\underline{H}_2$OC(O)Su), 6.63 (2H, m, —N$\underline{H}$CO—), 6.70 (4H, s, —C$\underline{H}$=C$\underline{H}$—)

What is claimed is:

1. A branched hetero polyfunctional polyoxyalkylene compound represented by formula (1):

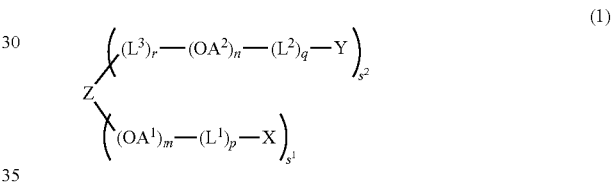

wherein Z represents a hydroxyl group-removed residue of pentaerythritol or dipentaerythritol, OA$^1$ and OA$^2$ are an oxyalkylene group having 2 to 4 carbon atoms, L$^1$, L$^2$ and L$^3$ are an alkylene group or an alkylene group that contains an ester bond, a urethane bond, an amide bond, an ether bond, a carbonate bond, a secondary amino group or a urea bond, OA$^1$ and OA$^2$ and L$^1$, L$^2$ and L$^3$ may be same or different from one another in one molecule; X and Y are different from each other and represent a functional group capable of a chemical reaction; m and n are an average number of moles of the oxyalkylene group added, m represents 5 to 1,000, n repre- (p7)

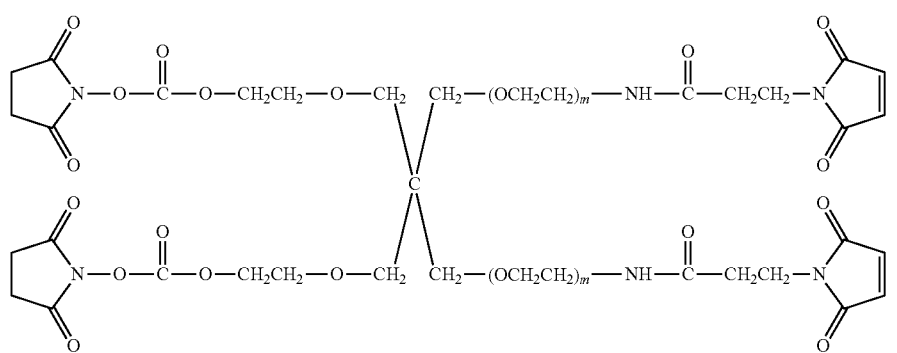

m = about 223 sents 0 to 1,000, and p, q and r represent 0 or 1; and $s^1$ is an integer of 2 or more and $s^1+s^2=4$ or 6;

wherein the functional group capable of a chemical reaction is selected from the group consisting of:

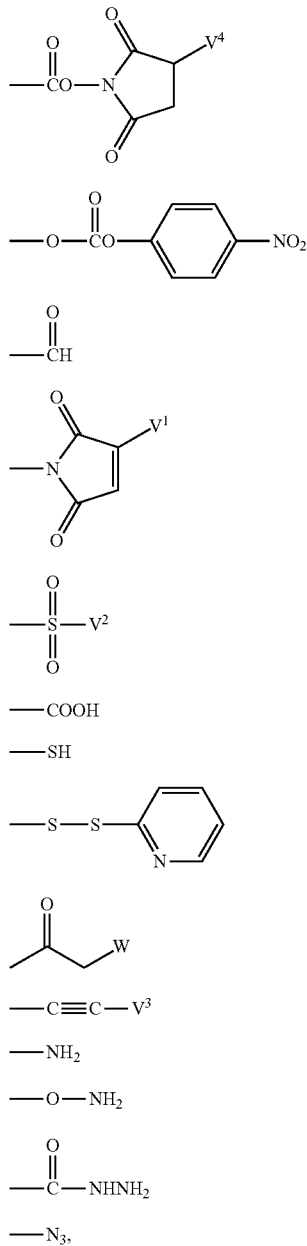

wherein $V^1$ and $V^3$ represent a hydrocarbon group having 1 to 5 carbon atoms; $V^2$ represents a hydrocarbon group having 1 to 10 carbon atoms that may contain a halogen atom; and $V^4$ represents a hydrogen atom or a sulfonyl group, and wherein the alkylene group that contains an ester bond, a urethane bond, an amide bond, an ether bond, a carbonate bond, a secondary amino group or a urea bond is selected from the group consisting of:

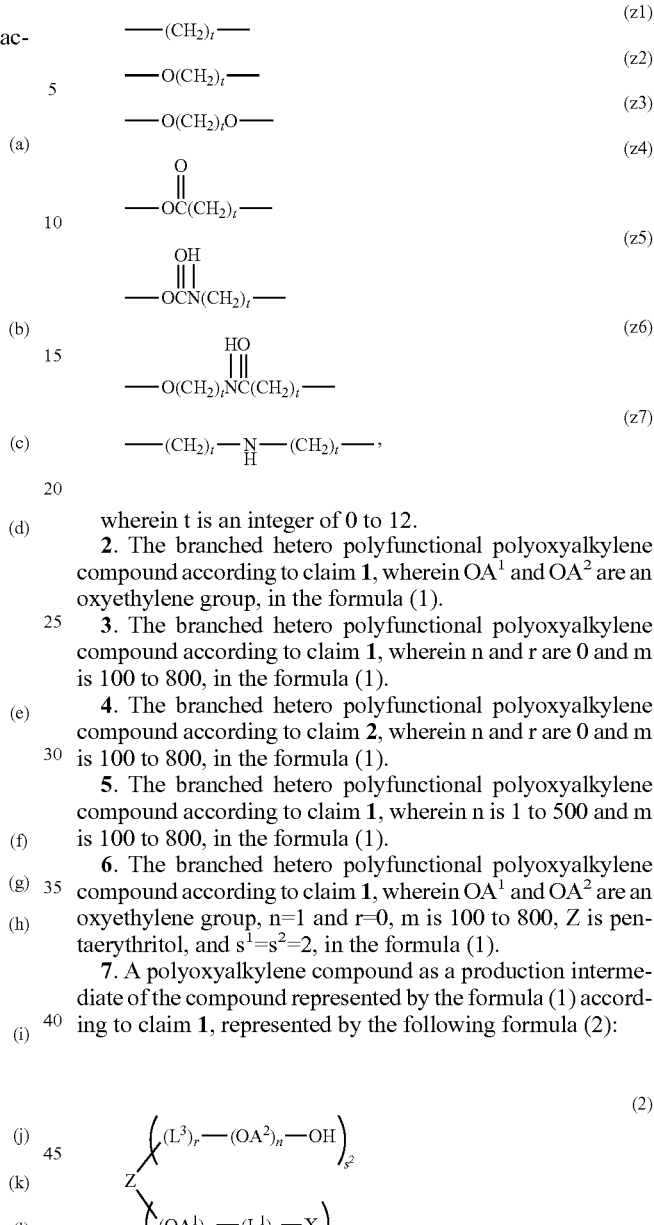

wherein t is an integer of 0 to 12.

2. The branched hetero polyfunctional polyoxyalkylene compound according to claim 1, wherein $OA^1$ and $OA^2$ are an oxyethylene group, in the formula (1).

3. The branched hetero polyfunctional polyoxyalkylene compound according to claim 1, wherein n and r are 0 and m is 100 to 800, in the formula (1).

4. The branched hetero polyfunctional polyoxyalkylene compound according to claim 2, wherein n and r are 0 and m is 100 to 800, in the formula (1).

5. The branched hetero polyfunctional polyoxyalkylene compound according to claim 1, wherein n is 1 to 500 and m is 100 to 800, in the formula (1).

6. The branched hetero polyfunctional polyoxyalkylene compound according to claim 1, wherein $OA^1$ and $OA^2$ are an oxyethylene group, n=1 and r=0, m is 100 to 800, Z is pentaerythritol, and $s^1=s^2=2$, in the formula (1).

7. A polyoxyalkylene compound as a production intermediate of the compound represented by the formula (1) according to claim 1, represented by the following formula (2):

wherein Z represents a hydroxyl group-removed residue of pentaerythritol or dipentaerythritol, $OA^1$ and $OA^2$ are an oxyalkylene group having 2 to 4 carbon atoms, $L^1$ and $L^3$ are an alkylene group or an alkylene group that contains an ester bond, a urethane bond, an amide bond, an ether bond, a carbonate bond, a secondary amino group or a urea bond, $OA^1$ and $OA^2$ and $L^1$ and $L^3$ may be the same or different from one another in one molecule; X represents a functional group capable of a chemical reaction or a protected functional group; m and n are an average number of moles of the oxyalkylene group added, m represents 5 to 1,000, n represents 0 to 1,000, and p and r represent 0 or 1; and $s^1$ is an integer of 2 or more and $s^1+s^2=4$ or 6.

* * * * *